United States Patent [19]

Bennetto et al.

[11] Patent Number: 4,970,145
[45] Date of Patent: Nov. 13, 1990

[54] IMMOBILISED ENZYME ELECTRODES

[75] Inventors: Hugh P. Bennetto; Gerard M. Delaney; Jeremy R. Mason; Christopher F. Thurston; John L. Stirling, all of London; David R. DeKeyzer, Old Woking, all of Great Britain

[73] Assignee: Cambridge Life Sciences plc, Cambridge, Great Britain

[21] Appl. No.: 146,278

[22] Filed: Jan. 20, 1988

Related U.S. Application Data

[63] Continuation of PCT GB87/00365 filed on May 27, 1987.

[30] Foreign Application Priority Data

May 27, 1986 [GB] United Kingdom ................ 8612861

[51] Int. Cl.$^5$ ........................... C12M 1/40; C12N 9/04
[52] U.S. Cl. ........................................ 435/14; 435/817; 435/25; 435/174; 435/291; 435/176; 435/177; 435/680; 435/181; 204/403
[58] Field of Search .................... 435/817, 14, 25, 174, 435/288, 291, 176, 177, 180, 181, 311; 204/1 T, 403

[56] References Cited

U.S. PATENT DOCUMENTS

| 4,229,490 | 10/1980 | Frank et al. | 5/12 |
| 4,415,666 | 11/1983 | D'Orazio | 435/25 |
| 4,820,399 | 4/1989 | Senda et al. | 204/403 |

FOREIGN PATENT DOCUMENTS

| 0026995 | 4/1981 | European Pat. Off. | |
| 0048090 | 3/1982 | European Pat. Off. | 435/4 |
| 0078636 | 11/1983 | European Pat. Off. | |
| 2903216 | 8/1979 | Fed. Rep. of Germany | 435/817 |
| 0041191 | 4/1979 | Japan | 435/817 |
| 0124060 | 9/1980 | Japan | 204/403 |
| 56-163447 | 3/1982 | Japan . | |
| 0070448 | 4/1982 | Japan | 435/4 |

OTHER PUBLICATIONS

Aston and Turner, *Biosensors and Biofuel Cells*, Biotechnology and Genetic Engineering Reviews, 1, Feb. 1984, 89–120.
Graham Davis, *Electrochemical Techniques for the Development of Amperometric Biosensors*, Biosensors, 1, 161–178 (1985).

Jonsson and Gorton, *An Amperometric Glucose Sensor Made by Modification of a Graphite Electrode Surface with Immobilized Glucose Oxidase and Adsorbed Mediator*, Biosensors, 1, 355–369 (1985).
Cass et al., *Ferrocene—Mediated Enzyme Electrode for Amperometric Determination of Glucose*, Analyt. Chem., 56, 667–673 (1984).
Ianiello et al., *Differential Pulse Voltammetric Study of Direct Electron Transfer in Glucose Oxidase Chemically Modified Graphite Electrodes*, (1982), Analyt. Chem., 54, 1098–1101.
Ianiello and Yacynych, *Immobilized Enzyme Chemically Modified Electrode as an Amperometric Sensor*, (1981), Analyt. Chem., 53, 2090–2095.
Tarasevich, Bioelectrochemistry 10, 231–295 (1985).

*Primary Examiner*—Robert A. Wax
*Assistant Examiner*—Janelle D. Waack
*Attorney, Agent, or Firm*—St. Onge Steward Johnston & Reens

[57] ABSTRACT

Enzyme electrodes are disclosed which are capable of responding amperometrically to the catalytic activity of the enzyme in the presence of its respective substrate and comprising the enzyme immobilized or adsorbed onto the surface of an electrically conductive support member which consists of or comprises a porous layer of resin-bonded carbon or graphite particles, said particles having intimately mixed therewith, or deposited or adsorbed onto the surface of the individual particles prior to bonding to form said layer, a finely divided platinum group metal, thereby to form a porous, substrate layer onto which said enzyme is adsorbed or immobilized and comprising a substantially heterogeneous layer of resin-bonded carbon or graphite particles, with said platinum group metal dispersed substantially uniformly throughout said layer. The preferred substrate materials are resin bonded platinized carbon paper electrodes comprising platinized carbon powder particles having colloidal platinum adsorbed on the surface of the particles and bonded onto a carbon paper substrate using a synthetic resin, preferably polytetrafluoroethylene, as the binder. The preferred enzyme electrodes are glucose oxidase electrodes comprising glucose oxidase adsorbed or immobilized onto the surface of the substrate.

24 Claims, 15 Drawing Sheets

GLUCOSE ENZYME ELECTRODE
(PROTOTECH SUBSTRATE)

FIG. 4 SENSITIVITY OF PROTOTECH BASED GLUCOSE SENSOR TO AMBIENT OXYGEN TENSION

STABILITY OF PROTOTECH BASED GLUCOSE SENSOR STORED WET AT ROOM TEMPERATURE—RESPONSE TO 5mM GLUCOSE

COMPARISON BETWEEN LACTATE ENZYME
ELECTRODES CONSTRUCTED USING
PROTOTECH & PRIOR ART-TYPE ELECTRODES
(CARBODIIMIDE IMMOBILISATION)

FIG.10 GALACTOSE ENZYME ELECTRODE (PROTOTECH SUBSTRATE)

RESPONSE TO LACTOSE OF A PROTOTECH ELECTRODE INCORPORATING IMMOBILISED GLUCOSE OXIDASE AND $\beta$-GALACTOSIDASE.

GLUCOSE ENZYME ELECTRODE CONSTRUCTED
USING PLATINISED CARBON PAPER WITH
POLY VINYL ACETATE AS BINDER

IMMOBILIZED ENZYME ELECTRODES

Continuation under 35 U.S.C. 365(c) of International Application No. PCT/GB 87/00365 filed May 27, 1987.
Priority: British Patent Application No. GB 8612861 filed May 27, 1986.

FIELD OF THE INVENTION

This invention relates to enzyme electrodes, comprising an enzyme immobilised onto an electrically conductive substrate, and which respond amperometrically to the catalytic activity of the enzyme in the presence of its respective substrate. Particularly, but not exclusively, the invention relates to enzyme electrodes which may be used to detect glucose levels both in vitro and in vivo, and which comprise an electrically conductive substrate onto which is immobilised an oxidoreductase e.g. a glucose oxidase, the electrode responding amperometrically to the catalytic activity of the immobilised enzyme when introduced into a glucose-containing sample.

BACKGROUND AND PRIOR ART

The advantages of amperometric biosensors which incorporate an enzyme as a biocatalyst have been reviewed in some detail by Aston and Turner, (1984) Biotech. Genet. Eng. Rev. (ed. G. Russell), 1, 89–120, Intercept, Newcastle-upon-Tyne, and by Davis G., (1985) Biosensors, 1, 161–178. They vary in the mode of signal transduction, and different types may be loosely classified as (a) those in which the electrical response arises from the oxidation of a product of the enzyme reaction at an electrode; (b) "mediator assisted", in which electrons are transported from the enzyme to the electrode with the aid of an oxidation-reduction ("redox") reagent, or (c), "direct electron transfer" (DET), in which no such mediator assistance is required.

CATEGORY (A)

This category may be illustrated with reference to the action of certain oxidases (e.g. glucose, oxidase, alcohol oxidase) which enzymes produce hydrogen peroxide according to the reaction:

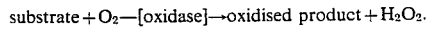

substrate+$O_2$—[oxidase]→oxidised product+$H_2O_2$.

In this method, the peroxide is oxidised at an electrode poised at a fixed potential:

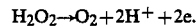

$H_2O_2 \rightarrow O_2 + 2H^+ + 2e$.

An electrical signal is produced following transfer of electrons from the peroxide to the electrode, and under suitable conditions the enzyme-catalysed flow of current is proportional to analyte concentration.

Numerous devices for determination of glucose have been described, but most of them have limitations with respect to the reproducibility and speed of response, and the range of glucose concentration accessible. Some of the moderately successful commercial methods rely on utilisation of peroxide as outlined above, where glucose is the substrate and the oxidised product is glucono-1,5-lactone. Other methods depend on secondary reactions of peroxide (e.g. colorimetric assays) or a physico-chemical measurement such as conductance. However they are generally slow in response, and have the disadvantage of being rather sensitive to the oxygen tension in the samples, which may vary considerably; at low oxygen tensions the upper limit for linearity of current response may be lower than desired for simple, accurate assays. Similar considerations apply to indirect assay methods for substrates other than glucose.

CATEGORY (B)—MEDIATOR-ASSISTED BIOSENSORS

In these devices, the enzyme is maintained in a reduced ("electron-rich") state as a result of its reaction with the substrate, which is the analyte whose concentration is to be measured. A requirement for a practicable sensor is the establishment of electrical coupling between the source of electrons (some electron-rich "active site" within the enzyme) and the electrode itself. But since active sites tend to reside within clefts or folds within the macromolecular enzyme structure, access to them is wholly or partially blocked, and it is therefore a matter of some difficulty to establish an electrical connection which is sufficiently effective for reliable and sensitive signal transduction. Transfer of electrons between an enzyme and an electrode may, however, be facilitated by inclusion of an electron carrier or "mediator", which in the oxidised form takes up electrons from the enzyme, and then, in the reduced state, transports them to the electrode, where it becomes reoxidised.

The use of mediators may be illustrated by recently-described bio-sensors which use glucose oxidase immobilised on a carbon electrode. One design utilises covalently bound enzyme immobilised by the cyanuric chloride method (Jonsson and Gorton, 1985, Biosensors, 1, 355–369) which, it is claimed, confers good stability (several months). However, the sensor has serious disadvantages in that the mediator used, N-methyl phenazinium ion (phenazine methosulphate), is unstable and is also easily washed out, needing daily replacement in use. The electrode is also sensitive to oxygen concentration, though it was demonstrated that the electrochemical transduction via the mediator competes well with the oxygen reduction reaction. Another biosensor which also incorporates immobilised glucose oxidase uses ferrocene or one of its derivatives as mediator: Cass et al., (1984) Analyt. Chem. 56, 667–673 and EP-A-0 078 636. The transfer of electrons to the electrode via the mediator proceeds as follows:

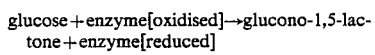

glucose+enzyme[oxidised]→glucono-1,5-lactone+enzyme[reduced]

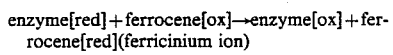

enzyme[red]+ferrocene[ox]→enzyme[ox]+ferrocene[red](ferricinium ion)

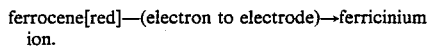

ferrocene[red]—(electron to electrode)→ferricinium ion.

Mechanistic details of operation of this electrode are not clear: in particular, it is not explained how the very insoluble reduced form of ferrocene carries charge to the electrode to maintain cyclic mediator activity (though this objection might not apply for ionic ferrocene derivatives). Moreover its response is rather sluggish considering the potentially very rapid response which might have been anticipated from the known rates of the enzymatic reactions involved, and the electrode has a limited lifetime, attributable to the limited stability of the enzyme.

The use of a mediator in signal transduction has several attendant disadvantages: the possibility of it leaching out from the region containing the biocatalyst, limitations to diffusion of oxidised and/or reduced forms, and inherent instability of the mediator itself.

CATEGORY (C)—DIRECT ELECTRON TRANSFER (DET) BIOSENSORS

The possibility of constructing a biosensor without the inclusion of a mediator has been suggested in a recent review on bioelectrocatalysis: Tarasevich, (1985) Bioelectrochemistry 10, 231–295. Such devices may be referred to as "reagentless" or "mediatorless". Examples of mediatorless enzyme electrodes are cited in Tarasevich's review, but they incorporate conducting organic polymers e.g. containing structural units similar to that of methyl viologen and/or conducting organic salts such as NMP+TCNQ−(N-methyl phenazinium tetracyano-4-quinodimethane) which modify the properties of the electrode and fulfil the role of mediators. Many of the methods of electron transduction from redox proteins via modified electrodes also fall into this category.

The intrinsic instability of many conducting organic polymers and salts is noted. Thus the activity of the NMP/TCNQ-modified electrode used in an alcohol biosensor has a half-life of about 15 days. Such electrodes are also oxygen sensitive.

According to the published evidence it appears that few truly mediatorless enzyme electrodes have yet been devised, though many unsuccessful attempts have been recorded, mostly using carbon base electrodes. Recent literature on the use of glucose oxidase (Jonsson and Gorton, loc. cit.) suggests that the main problem lies in the immobilisation of an enzyme, which tends to inhibit its electron transfer capabilities because of steric or other limitations, thus necessitating the inclusion of a mediator.

There are some rare examples of very active oxidases immobilised on carbon or platinum. For instance, Ianiello et al. (1982) Analyt. Chem. 54, 1098–1101, describe mediatorless sensors in which glucose oxidase and L-amino acid oxidase are covalently bonded to a graphite electrode by the cyanuric chloride method. However, the enzyme electrodes have a limited working lifetime of 20 to 30 days: Ianiello and Yacynych, (1981) Analyt. Chem. 53, 2090–2095. No information on the oxygen sensitivity of the electrodes is given.

Numerous biosensors operating according to the above principles, especially glucose sensors, have been disclosed in the prior art, and a representative selection has already been acknowledged; but for present purposes one disclosure has to be considered as particularly relevant, viz: Matsushita Electric Appliance Industry Company, Japanese Unexamined Patent Publication No. 56-163447. This discloses an indirect glucose electrode, i.e. in which hydrogen peroxide, produced by the oxidation of glucose in the presence of glucose oxidase:

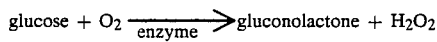
glucose + $O_2$ $\xrightarrow{\text{enzyme}}$ gluconolactone + $H_2O_2$ is oxidised at the surface of a platinum electrode

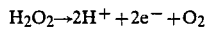
$H_2O_2 \rightarrow 2H^+ + 2e^- + O_2$ to produce an oxidation current proportional to the substrate (glucose) concentration of the sample. The electrode comprises an electrically conductive carbon base supporting a layer of immobilised enzyme, e.g. an immobilised glucose oxidase. The electrically conductive base itself is of moulded graphite containing up to 10 parts by weight of a fluorocarbon resin as a binder, and onto which is desposited, e.g. electrolytically or by vapour deposition, a thin (less than 1 μm) film of platinum. The invention allegedly avoids the problems associated with the immobilisation of the enzyme directly onto the platinum surface and produces an enzyme electrode allegedly characterised by rapid response times (5 seconds), high sensitivity and durability. However, recent experimental work with such electrodes has failed to elicit such benefits.

OBJECT OF THE INVENTION

Accordingly a need still exists for an enzyme electrode, a particularly but not exclusively for use in glucose biosensors, which is reliable and reproducible, which shows a rapid response and high sensitivity, and which has good long term stability.

SUMMARY OF THE INVENTION

In accordance with the present invention, a novel carbon substrate is used for an enzyme electrode which allows the enzyme, e.g. glucose oxidase, to be affixed to the electrode in a more advantageous manner which allows construction of an amperometric sensor of much-improved response and stability. This improved enzyme electrode does not require the use of a mediator reagent (although one can be added if desired), and is found to work in the presence of very low levels of dissolved oxygen. It gives large responses, e.g. current densities of hundreds of microamperes per square cm (apparent area of electrode) in a 10 mM glucose solution; this is believed to be much bigger than in any previous amperometric enzyme biosensor, and can be used to advantage in manufacture of micro-probe biosensors of less than 1 $mm^2$ electrode area producing 0 to 100 nanoamperes. The electrode can also be constructed using very small quantities of immobilised enzyme. It responds to glucose much faster than any known glucose sensor, typically 1 to 2 seconds in the absence of a protective membrane, and 10 to 30 seconds with a membrane. It has remarkable stability when stored wet, even at room temperature; electrodes show good response even after many months. They have an extended working range, require a substantially lower operating potential than normal (325 mV as against the more usual 650 mV), and exhibit remarkably low background at the operating potential.

BRIEF DESCRIPTION OF THE DRAWINGS

The results obtained using enzyme electrodes according to the invention are discussed in detail below and are illustrated graphically in the accompanying drawings, in which.

DETAILED DESCRIPTION

Figure 1:
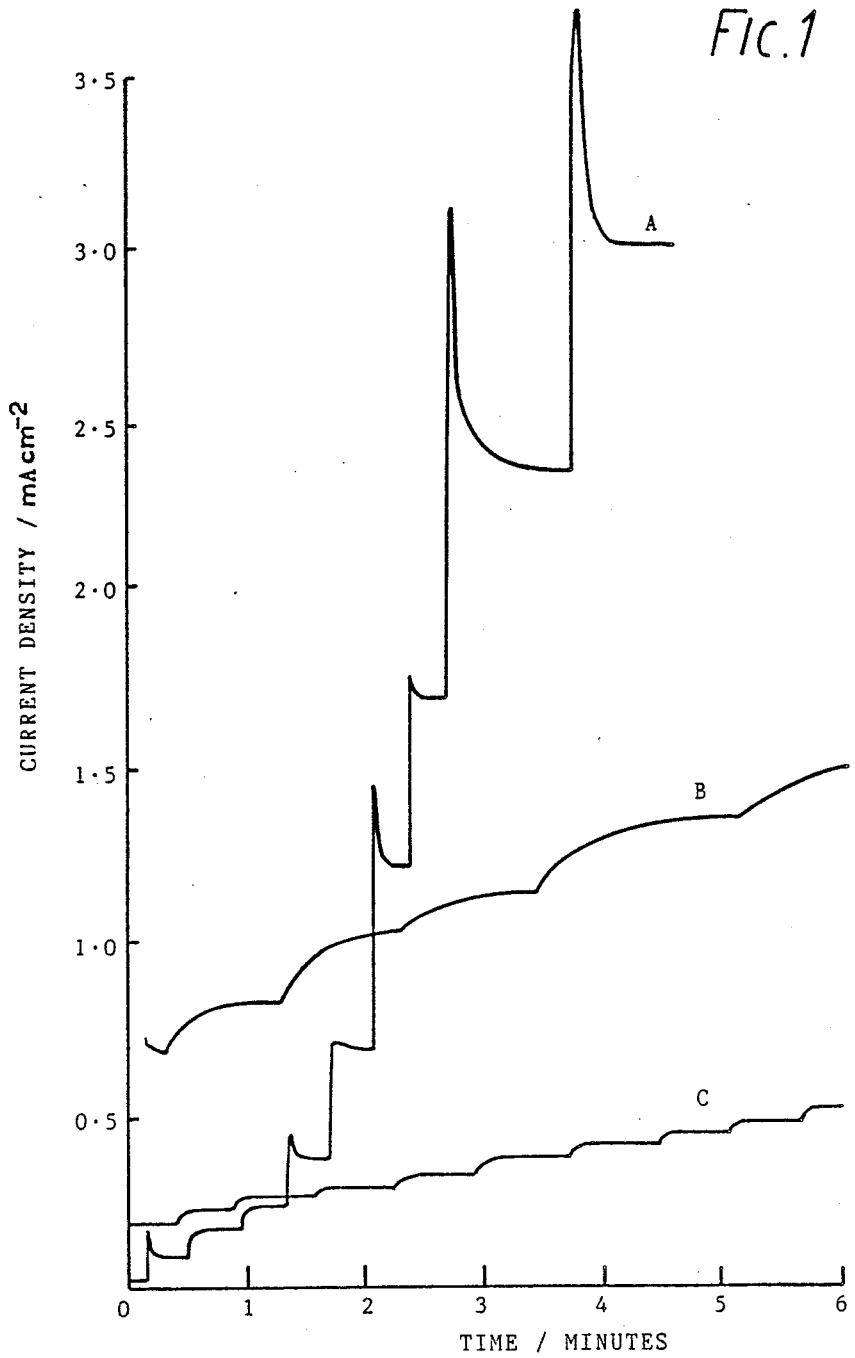
FIG. 1 illustrates the response of a glucose oxidase electrode according to the invention in comparison with glucose oxidase immobilised onto other types of carbon electrode.

The basis of the present invention is an enzyme electrode or biosensor comprising an enzyme immobilised onto the surface of an electrically conducting support member which consists of or comprises a porous layer of resin-bonded carbon or graphite particles, said particles having intimately mixed therewith, or deposited or adsorbed onto the surface of the individual particles prior to bonding to form said layer, a finely divided platinum group metal, thereby to form a porous, substrate layer onto which said enzyme is adsorbed or immobilised and comprising a substantially heterogeneous layer of resin-bonded carbon or graphite particles, with said platinum group metal dispersed substantially uniformly throughout said layer. Thus, in specific contrast to the layered, non-heterogeneous platinised carbon support disclosed in Japanese Published Application No. 56-163447, the electrode according to this invention consists of or comprises a substantially heterogeneous layer of resin-bonded carbon or graphite particles with said platinum group metal dispersed substantially uniformly throughout that layer. Preferably, the resin bonded carbon powder layer is formed by resin-bonding carbon powder particles onto which colloidal platinum or palladium has been deposited or adsorbed, prior to moulding to form the substrate. Preferred resin binders used in moulding the platinised carbon particles to form the electrode substrate used in this invention are fluorocarbon resins, especially polytetrafluoroethylene.

Referring to the construction of the enzyme electrode of this invention in more detail, the preferred electrode comprises, as indicated, an electrically conductive base consisting of or comprising a layer of resin bonded carbon powder having a platinum group metal, e.g. platinum or palladium, adsorbed onto the surface of the powdered particles prior to bonding.

As the carbon powder there may be used any suitable carbon or graphite powder which readily permits the subsequent immobilisation of the enzyme, and to this end, carbon powders should be used having a high density of functional groups, such as carboxylate, amino and sulphur-containing groups, on the surface, as opposed to the more vitreous and glassy carbons, which bind enzymes only poorly. Particle size may range from 3 to 50 nm, more usually 5 to 30 nm.

Platinum (or palladium) may be deposited on the carbon particles in any convenient fashion, e.g. vapour phase deposition, electrochemical deposition or simple adsorption from colloidal suspension (which is preferred) to give platinum group metal loadings of from 1 to 20% by weight, based on the weight of carbon, preferably from 5 to 15%. These limits are, however, practical rather than critical. Below about 1% platinum group metal the output signal falls to a level which, in practical terms, is too low to be measured except by very sensitive apparatus. Above about 20%, the loading of platinum group metal becomes uneconomic, with little additional benefit in terms of response time, sensitivity etc. Indeed with extremely high metal loadings the sensitivity begins to fall. In the preferred technique the carbon powder is platinised or palladised by the oxidative decomposition of a platinum or palladium compound such as chloroplatinic acid, or more preferably still a complex of platinum or palladium with an oxidisable ligand, in the presence of the carbon powder, thereby to deposit colloidal size platinum or palladium direct onto the surface of the carbon particles, in the manner taught, for example, in GB-A-1,357,494, U.S. Pat. Nos. 4,044,193 and 4,166,143.

Following platinisation or palladisation the platinised or palladised carbon powder is moulded using a suitable water-repellent bonding resin, preferably a fluorocarbon resin such as polytetrafluoroethylene to form either a completely self-supporting porous moulded structure consisting essentially of said resin bonded platinised or palladised carbon powder particles, or more usually a porous moulded surface layer of such resin-bonded particles bonded to an electrically conductive substrate, e.g. of metal, carbon or graphite. A particularly preferred substrate material for the moulded, resin-bonded platinised carbon layer is carbon paper as taught by U.S. Pat. No. 4,229,490, or an open pore carbon cloth as taught by U.S. Pat. No. 4,293,396. In order to retain maximum porosity the amount of resin used as the binding agent should be the minimum required to provide mechanical integrity and stability to the electrode layer, such layer usually having a thickness no more than about 0.1 to 0.5 mm, although greater thicknesses may be employed. Subject to the requirements of structural integrity, mechanical strength, and porosity, amounts of binding resin are not critical and may range from as little as 5 or 10% by weight, based on the amount of platinised or palladised carbon powder, up to as much as 80%, but with the amount more usually in the range 30 to 70% by weight. A variety of resins may be used, including resins which are conducting or semi-conducting, but preferred are synthetic fluorocarbon resins, particularly polytetrafluoroethylene. In view of the small but essential requirement for oxygen in the oxidation process it is essential that the binder be permeable to oxygen. To this end the binder should have a minimum solubility towards oxygen at atmospheric pressure of at least $2 \times 10^{-3}$ cm$^3$ O$_2$ (measured at standard temperature and pressure) per cm$^3$ of polymer.

Suitable binders and their known oxygen solubilities taken from The Polymer Handbook (Ed. J. Brandrup and E. H. Immergut) 1st Ed. (1967), Interscience, include:

|  | $S \times 10^2$ (cm$^3$) |
| --- | --- |
| Polytetrafluoroethylene (PTFE) | 0.276 |
| Fluorocarbon polymers other than PTFE | Variable, 0.2 upwards |
| Polyethylmethacrylate | 8.6 |
| Polystyrene | 18.2 (calculated) |
| Polyvinyl acetate | 6.3 |
| Polyvinyl chloride | 2.92 |
| Polycarbonate | 0.51 |
| Poly(4-methylpentene-1) | 24.3 |
| Polyisoprene | 10.3 |
| Polychloroprene | 7.5 |
| Poly 1,3-butadiene | 9.7 |
| Silicone rubber | 31.1 |

The preferred enzyme electrode substrates used in accordance with this invention are, in fact, commercially available materials sold under the trade mark Prototech by the Prototech Company of Newton Highlands, Mass., and used heretofore as electro-catalytic gas diffusion electrodes in fuel cells. The preparation of such materials is described in detail in U.S. Pat. Nos. 4,044,193, 4,166,143, 4,293,396 and 4,478,696, to which reference should be made for full details. In broad detail, however, colloidal platinum with a particle size in the range 15 to 25 Angstroms (1.5 to 2.5 nm) is adsorbed onto the surface of powdered carbon (particle size 50 to 300 Angstroms: 5 to 30 nm), for example, by formation of a platinum sol in situ in the presence of powdered carbon which acts as a nucleating agent for the sol. The platinised carbon particles are then moulded onto an electrically conductive supporting structure e.g. a sheet of carbon paper, using a synthetic resin binder, preferably a fluorinated hydrocarbon resin, and especially polytetrafluoroethylene.

In an alternative, disclosed in U.S. Pat. No. 4,293,396, the platinised carbon particles are impregnated into a preformed porous carbon cloth and bonded therein using the fluorocarbon resin, preferably polytetrafluoroethylene. It is to be understood, however, that the present invention is not limited to the use of Prototech materials, but embraces other similar substrate materials comprising resin-bonded and moulded platinised or palladised carbon powder. In particular, it is contemplated that there also may be used materials of the type disclosed as fuel cell electrodes in U.S. Pat. No. 4,229,490, that is to say carbon paper electrodes of the type comprising a carbon paper support member, preferably impregnated with a water-repellent resin such as polytetrafluoroethylene, and onto which is deposited, e.g. by screen printing, a resin bonded catalyst layer comprising a uniform mixture of platinum black and carbon or graphite particles bonded with a water-repellent resin, preferably again polytetrafluoroethylene.

The immobilisation of the enzyme on the surface of the resin-bonded, platinised or palladised carbon substrate can be carried out using a variety of well established immobilisation techniques, for example, covalent bonding with a carbodiimide or a carbonyldiimidazole reagent, covalent bonding with 1,6-dinitro-3,4-difluorobenzene (DFDNB), or cross-linking with glutaraldehyde.

Typical exemplary protocols for the immobilisation of the enzyme, glucose oxidase, are as follows:

A. Carbodiimide Treatment:
1. Cut out pieces of electrode of suitable size from the sheet of Prototech electrode material.
2. Immerse the electrodes in ethanol for about 5 minutes to ensure thorough wetting of the PTFE coated binder and backing.
3. Remove the electrodes from the ethanol and wash them thoroughly with distilled water to remove all traces of ethanol.
4. Prepare 5 ml (or less) of a 0.15M solution of 1-cyclohexyl-3-(2-morpholino)carbodiimide p-methyltoluene sulphonate in 0.1M pH 4.5 acetate buffer and place the electrodes in this for 90 minutes at room temperature. Gentle agitation with a mechanical shaker may be used. Should the electrodes float on the surface of the solution then they have not been sufficiently wetted, and the treatment should be repeated from step 2.
5. Remove the electrodes and wash them thoroughly with distilled water. Place them in a freshly prepared solution of glucose oxidase (5.0 mg/ml) in pH 5.6 acetate buffer for 90 minutes at room temperature with gentle mechanical shaking.
6. Remove the electrodes from the enzyme solution and rinse them thoroughly with 0.1M acetate buffer. The electrodes are now ready for use.
7. Store the electrodes at 4° C. in 0.1M pH 5.6 acetate buffer.

B. Carbonyldiimidazole Treatment:
1. Carry out step 1 above and omit steps 2 and 3.
2. Prepare a solution of N,N'-carbonyldiimidazole in anhydrous dimethyl formamide (40 mg/ml).
3. Place the electrodes in this solution for 90 minutes at room temperature with gentle mechanical shaking if desired.
4. Remove the electrodes from the solution and dry off the excess carbonyldiimidazole solution before placing them in a freshly prepared solution of glucose oxidase for a further 90 minutes.
5. Carry out steps 6 and 7 above.

C. DFDNB Treatment:
1. Carry out steps 1–3 under A above.
2. Wash the electrodes thoroughly in sodium borate buffer (0.1M, pH 8.5).
3. Prepare a solution of 1,6-dinitro-3,4-difluorobenzene in methanol (0.1021 g/5 ml) and place the electrodes in this for 10 minutes at room temperature.
4. Remove the electrodes and wash them thoroughly with borate buffer before placing them in a solution of glucose oxidase for a further 90 minutes at room temperature.
5. Carry out steps 6 and 7 under A above.

Other types of coupling agent may be used for the immobilisation process, including bifunctional agents of variable chain length, for example diimidates such as dimethylmalonimidate or dimethylsuberimidate.

In the alternative, it has been found that simple adsorption of the enzyme onto the resin-bonded platinised or palladised carbon powder support, i.e. without cross-linking, is effective with some enzymes, and in particular with glucose oxidase.

Usually, but not necessarily, the surface layer of immobilised enzyme will be physically protected by the application of a suitably porous, e.g. polycarbonate, film or membrane which must, of course, be permeable by the enzyme substrate (glucose) which is to be determined. Such membranes are somewhat disadvantageous in increasing the response time of the sensor, but nevertheless even with such a membrane the present sensors are capable of response times comparable with, and in many cases, substantially better than, conventional enzyme electrodes.

As already indicated, the invention relates particularly to glucose oxidase electrodes, i.e. in which the immobilised enzyme is a glucose oxidase, but it will be apparent that other oxidoreductases can be used, although not always with equivalent effect. This is not necessarily due to any inherent ineffectiveness of the enzyme, but to other factors. For example, in the determination of oxalic acid using oxalate oxidase the oxalic acid substrate itself undergoes electrochemical oxidation at the base electrode, thus largely masking any effect from the enzyme. However, other suitable oxidoreductases include lactate oxidase, galactose oxidase, cholesterol oxidase and other peroxide producing enzymes as well as combinations of immobilised enzymes, including combinations of a nonoxidase and an oxidase, the first acting on a substrate of interest to produce an oxidisable substrate for the oxidase, the latter acting on the oxidisable product to produce a measurable current which is proportional to the concentration of the substrate of interest. One such combination is the combination of beta-galactosidase and glucose oxidase (for the quantitative determination of lactose), or the combination of a beta-glucan depolymerising enzyme, beta-glucosidase and glucose oxidase (for the determination of beta-glucans).

Other types of sensor application include the use of enzymic or nonenzymic reagents or processes which interact with a primary substrate of interest in a precursor reaction, the resulting product including a substance which in turn acts as a substrate for an enzyme electrode according to this invention. Many examples of such precursor steps will be found in the field of immunochemical reactions, and methods of using such reactions in the construction of sensors, including immunosensors, utilizing enzyme electrodes according to the present invention will be apparent to those skilled in the art.

However, the primary application of the electrodes according to the invention will be as biosensors for the detection and/or quantitative measurement of an oxidisable substrate, especially glucose, in a sample, especially a clinical sample such as blood, serum, plasma, urine, sweat, tears and saliva.

Other possible, non-clinical applications include:
(a) fermentation monitoring,
(b) industrial process control,
(c) environmental monitoring, e.g. effluent and pollution control of liquids and gases,
(d) food testing,
(e) veterinary applications, particularly applications allied to the clinical applications suggested above.

In so far as bio- and other sensors incorporating an enzyme electrode material according to the present invention may comprise other structural elements, electrical leads, electrically non-conductive (insulating) supports or probes, etc., such elements in the construction are conventional and need not be described in detail. Suffice it to say that, where, as will usually be the case, the electrode material is a paper thin sheet or wafer, the biosensor will usually include an insulating support member or probe upon which the electrode material is mounted and by means of which the electrode material can be introduced into the sample. In such cases the actual size of the piece of electrode material may be quite small, no more than a few square millimeters, or even smaller. Electrical contact with the electrode material may be made in many ways, for example, by mounting the electrode material in face to face contact with an electrically conductive contact or terminal, e.g. of platinum, silver or other suitable conductor. Where the electrode material is of sufficient thickness and strength to be completely self-supporting, insulating supports or carriers for the electrode material can be dispensed with, and electrical leads connected directly to the surface of the electrode material.

Support members other than carbon paper can be utilised such as an electrically semi-conducting surface, for example the surface of a Field Effect Transistor (FET), or an electrically non-conductive surface. In the latter instance an electrical contact can be made directly to the platinum group metal resin bonded carbon or graphite layer.

The preparation of enzyme electrode materials according to this invention and their properties are illustrated by the following Examples.

EXAMPLE 1

(Comparative)

(Prior Art)

An enzyme electrode according to the prior art was prepared by the electrolytic deposition of a thin layer ($<1$ $\mu$m) of platinum onto the surface of an electrically conductive base consisting of a porous resin bonded carbon paper comprising conductive carbon black granules (Vulcan XC-72) having a nominal particle size of 30 nm and moulded onto a sheet of commercially available graphitised carbon paper using 10% by weight of polytetrafluoroethylene as the binder.

Glucose oxidase from *Aspergillus niger* was immobilised onto the surface of different samples of the platinised carbon paper by the carbodiimide treatment hereinbefore described, and by cross-linking with glutaraldehyde by treatment of the platinised surface of the electrode with aqueous glucose oxidase solution, drying and subsequent cross-linking of the deposited enzyme by exposure to glutaraldehyde at 25° C.

For subsequent testing the electrode material was subsequently cut into 2 mm diameter discs.

EXAMPLE 2

Glucose Electrode

Glucose oxidase from *Aspergillus niger* was immobilised onto platinised carbon paper sold under the trade name "Prototech" by Prototech Co., Massachussetts, U.S.A., and comprising platinised carbon powder particles (Vulcan XC-72) prepared in accordance with Example 1 of U.S. Pat. No. 4,044,193 by the deposition of colloidal platinum (particle size 1.5 to 2.5 nm) onto the surface of the carbon powder (nominal particle size 30 nm) by the oxidative decomposition of complex platinum sulfite acid (II) using $H_2O_2$, and subsequent moulding and bonding of the platinised carbon powder onto the surface of a commercial, graphitised carbon paper using approximately 50% by weight of polytetrafluoroethylene. The platinum loading of the final product is 0.24 mg.cm$^{-2}$.

Glucose oxidase was immobilised onto various samples of the Prototech material by the treatments hereinbefore described, viz: by treatment with carbodiimide, by carbonyldiimidazole treatment and by DFDNB treatment.

In separate experiments glucose oxidase was immobilised onto the Prototech material by cross-linking, with glutaraldehyde, and by simple adsorption, i.e. without cross-linking, by suspending the Prototech material in freshly prepared glucose oxidase solution (5.0 mg.ml$^{-1}$) in pH 5.6 acetate buffer for 90 minutes at room temperature. Alternatively, adsorption of the enzyme can conveniently be effected by a process of electrophoresis for which purpose the electrode base material is suspended at a positive potential in the enzyme solution for 60 minutes.

EXAMPLE 3

Utilising the carbodiimide treatment hereinbefore described the following enzymes were immobilised onto platinised carbon paper from Prototech, viz. a PTFE-bonded carbon paper produced from pre-platinised carbon powder (U.S. Pat. No. 4,044,193):
lactate oxidase
galatose oxidase
glucose oxidase/beta-galactosidase.

To further illustrate the benefits of the invention and the properties of the enzyme electrode materials of this invention in comparison with prior art electrodes, the enzyme electrode materials prepared as in the foregoing Examples were tested for amperometric response in a cell comprising a modified Rank oxygen electrode system (Rank Brothers, Bottisham, Cambridge) shown in the accompanying drawings and also in Analytica Chimica Acta, 183, (1986), 59–66. In this system the membrane is replaced by a carbon paper enzyme electrode (5 mm diam.) according to this invention which was retained on the platinum button electrode. The counter electrode (platinum foil) was inserted through the cell cover. The reference was a silver-silver chloride electrode. In some tests (with the protecting membrane, and unstirred solutions) a 2-electrode configuration was used; the counter/reference electrode was a surrounding chloridised silver ring. Usually the test solutions in pH 7.0 buffer were stirred magnetically, while the working electrode was held at a potential of 600 mV with respect to the reference with the aid of a potentiostat. When using the 2-electrode configuration a potential of 325 mV was employed. After allowing sufficient time for the background current to fall to a low level, substrate solution was injected from a syringe. The current response was recorded on a chart recorder. The results are presented graphically in the accompanying drawings.

Figure 15:
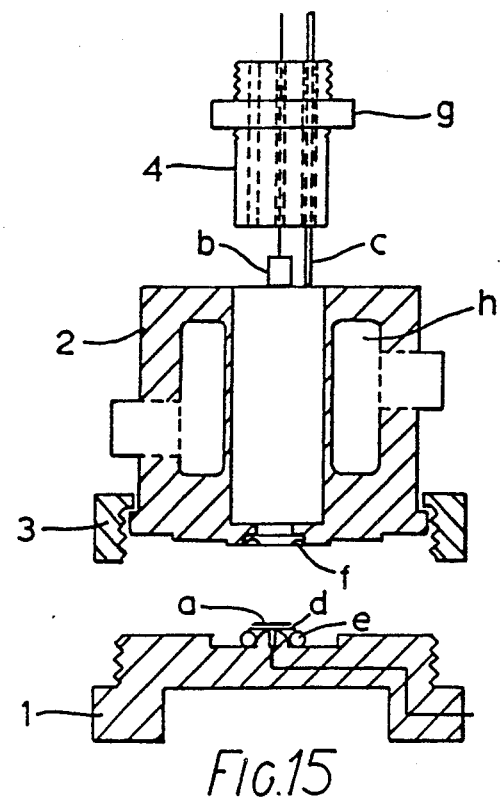
FIG. 15 illustrates the modified Rank electrochemical cell used in determining the operating characteristics of the electrodes according to the present invention.

Referring first of all to FIG. 15, much of the data presented herein were obtained using an electrochemical cell shown in FIG. 15. This comprises a two-part cell having a base (1) and an annular jacket (2) enclosing a water chamber (h), through which water may be circulated to control the temperature of the cell, the two parts being connected together by the captive threaded collar (3). Centrally located in the base (1) is a platinum contact (d) onto which is placed the test disc (a) of the paper electrode material comprising the immobilised enzyme, and which is held in place on the platinum contact by rubber O-ring seals (e) and (f) when the two parts of the cell are coupled together.

Inserted into the top of the cell, which of course will contain the enzyme substrate solution, is a stopper (4) supported by an adjustable collar (g) and in which are mounted a platinum counter electrode (b) and an Ag-/AgCl reference electrode (c). As indicated tests were carried out with the working electrode poised at 600 mV, the current output being measured from an electrode having an apparent surface area of 0.14 cm$^2$ exposed to the substrate solution. The results are expressed in the Figures in terms of current density, i.e. current output per unit area of electrode (a) exposed to the substrate.

Figure 16:
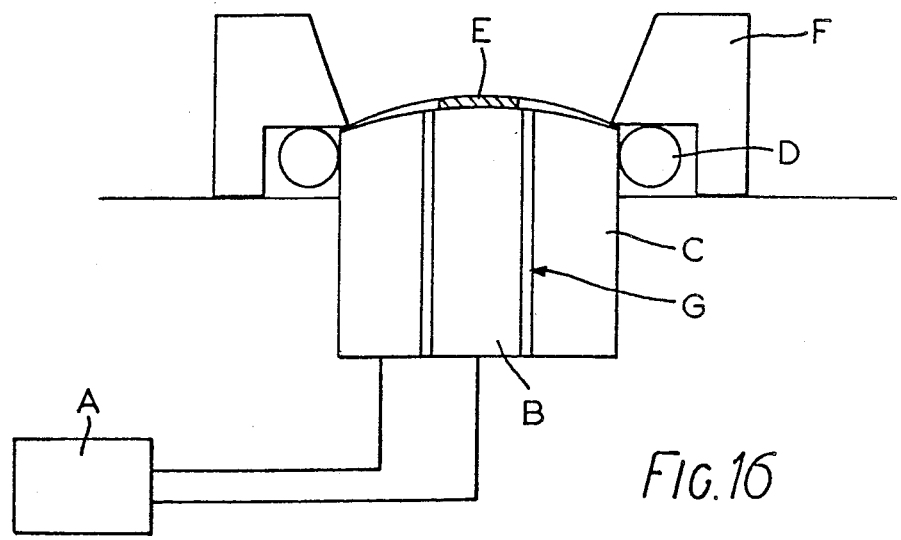
FIG. 16 illustrates the 2-electrode configuration used for some of the measurements.

Referring to FIG. 16, the platinum contact (B) is surrounded by the reference/counter electrode (C), being separated from it by an insulating sleeve (G). A porous polycarbonate membrane mounted on an "O" ring is used to hold the test disc (E) (the paper electrode material comprising the immobilised enzyme) onto the platinum contact. An open sample chamber (F) allows samples to be placed dropwise onto the membrane. The electrode cell is polarised at 325 mV and the current monitored via a potentiostat (A). The use of a 2-electrode configuration poised at 325 mV has advantages over the usual 3-electrode cell poised at 600 mV, namely convenience in use and a lower background current. However, the choice of one system over the other does not substantially affect the performance characteristics, such as storage stability, stability in use, linearity of response or oxygen dependence, of the electrodes of the invention.

The results obtained will be discussed in more detail below.

Linearity and time dependence of responses

Figure 2:
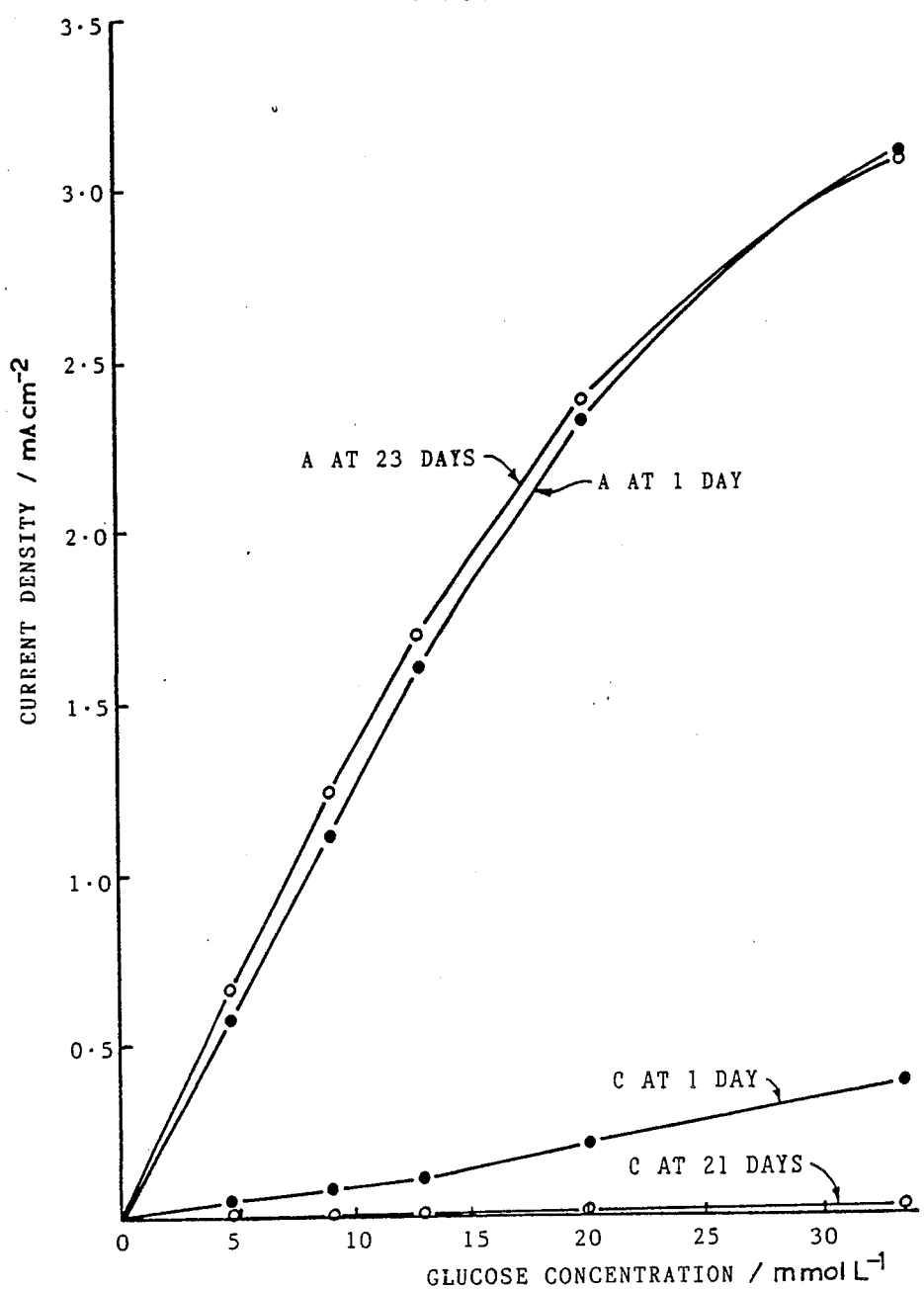
FIG. 2 is a first graph illustrating the stability of the glucose oxidase electrode.
Figure 3:
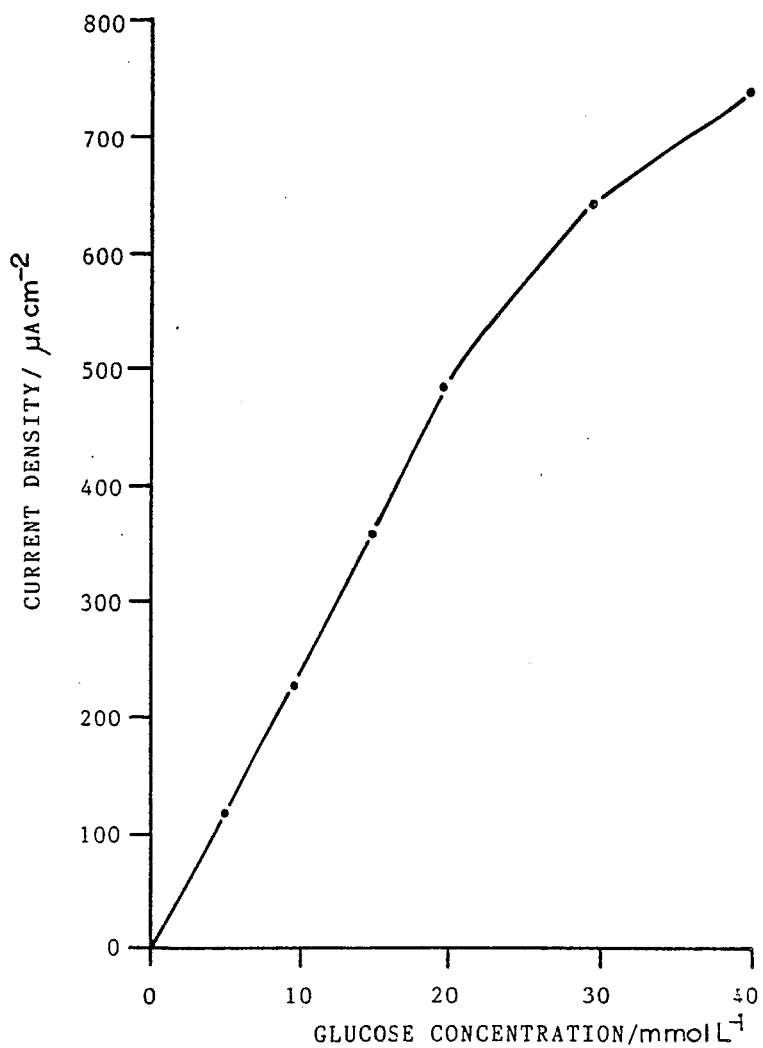
FIG. 3 is a second graph illustrating the response of the glucose oxidase electrode to a range of glucose concentrations.

In FIG. 1 of the accompanying drawings are shown typical examples of electrode response to sucessive additions of glucose giving final concentrations in the range 0 to 35 mM, using a 3-electrode cell under stirred conditions. All three electrodes A, B and C had glucose oxidase immobilised thereon by Method A above. Electrode A comprised an activated platinised carbon support according to the invention, viz: a moulded sheet of resin (polytetrafluoroethylene) bonded platinised carbon powder, sold under the trade mark Prototech; electrode B comprised an electrically conductive support cut from a section of graphite rod; electrode C comprised an electrically conductive support cut from a commercially available non-platinised carbon paper. As shown, electrodes B and C gave smaller, relatively sluggish responses, reminiscent of results with mediated sensors commonly presented in the literature. Electrode A gave more reliable and steady responses, with a response time of about 1 second. (The "spike" in the signal observed at the top of the initial response is in part an unimportant artefact resulting from the method of injection; the glucosedependent plateau is the signal of interest). All three electrodes gave a substantially linear response with respect to glucose concentration (FIG. 2, results shown for A, C only). This spans the range required for the direct analysis of glucose in blood (0 to 30 mM). Similar results obtained with type A electrodes using immobilisation procedure B above suggest this method gives even better linearity over an extended range.

As shown in FIG. 2, the response of electrode A was virtually unchanged after 23 days, but the response of the others deteriorated with time (as shown for electrode C). This type of behaviour was also observed for other methods of immobilisation described above, all of which could be used to make responsive and stable electrodes with carbon material used for A, but gave unsatisfactory electrodes with numerous other inactive carbon materials. The response time of A was also unchanged after 23 days, whereas other electrodes showed an increase in response time with initial response times of from about 23 to 30 seconds, increasing after 8 days to 2 to 3 minutes. Active electrodes (such as A) generally showed some fall in response during the first day, but the response then reached a plateau with respect to time. Electrodes of type A stored wet (pH 5.6) at 4° C. and tested at intervals over a 6-month period showed little change (after the first few days), and though there was some gradual deterioration after this period, the response at 12 months was still 70% of its original value.

FIGS. 1 and 2 show the current output of the electrode in $\mu A\ cm^{-2}$ at an operating potential of 600 mV, using the 3-electrode configuration shown in FIG. 15.

Figure 5:
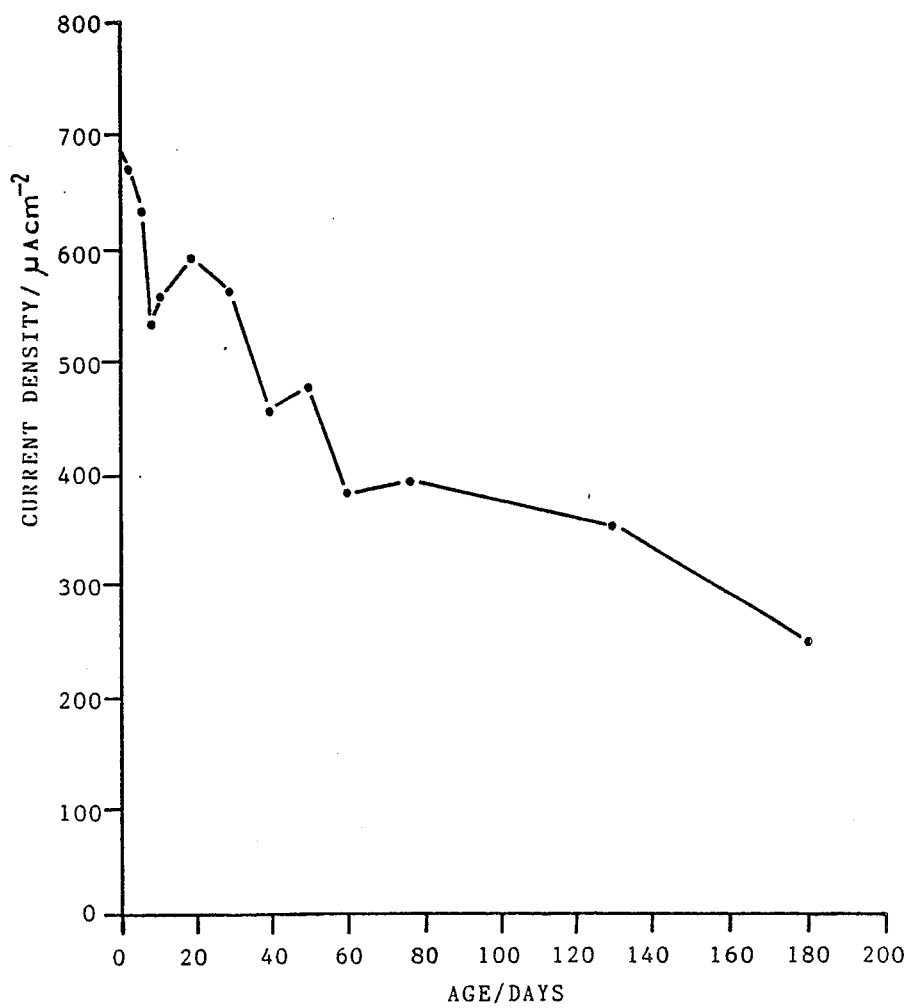
FIG. 5 is a graph illustrating the effect on the glucose oxidase electrode of storage at room temperature.
Figure 6:
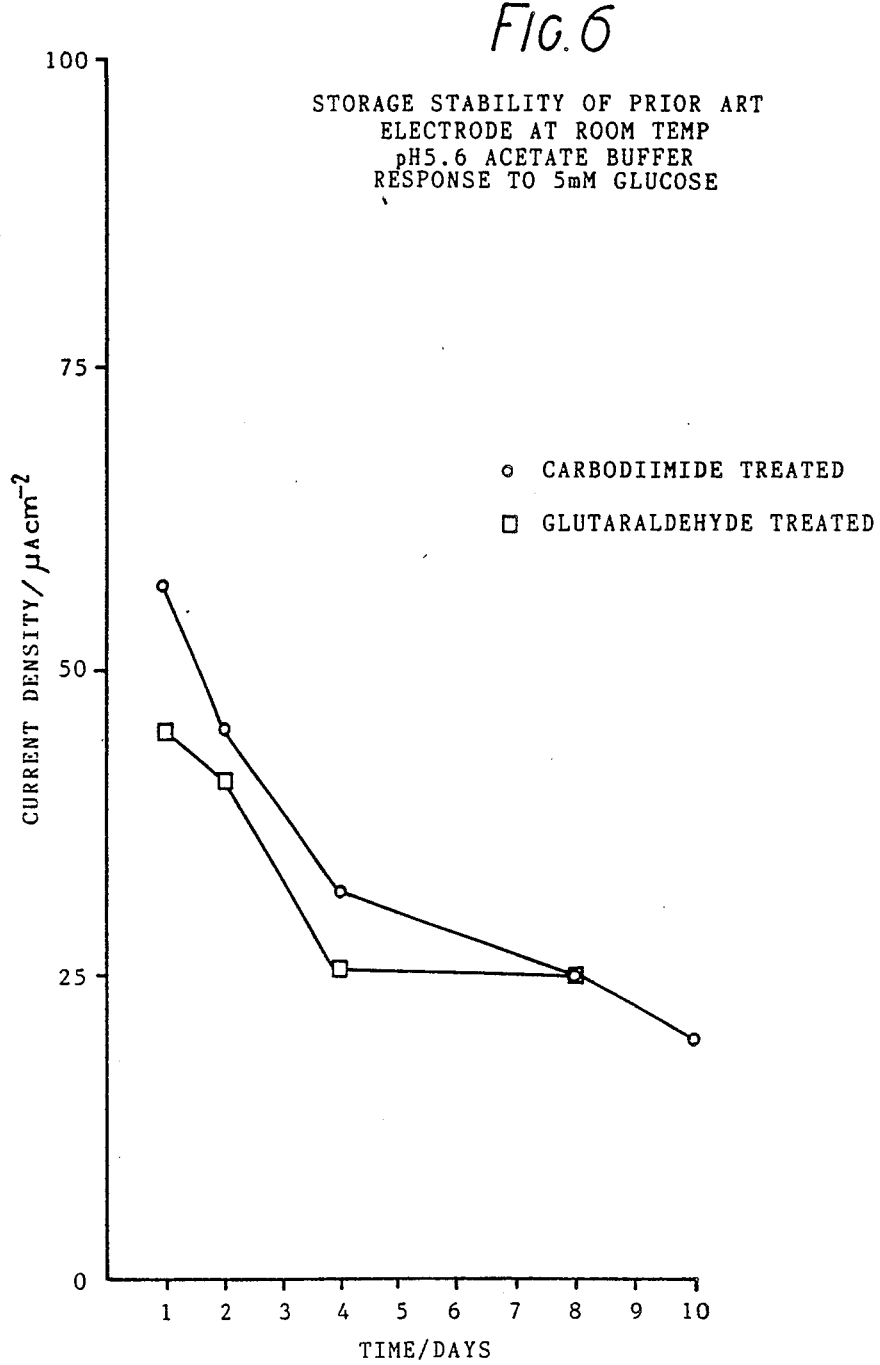
FIG. 6 is a comparative graph illustrating the effect on the prior art electrode of storage at room temperature.

The extended storage life and stability of the present electrodes is further illustrated by FIG. 5 which shows the response of the carbodiimide immobilised glucose oxidase electrode to 5 mM glucose after storage in pH 5.6 acetate buffer at room temperature during a period of 180 days. Comparative results for the prior art electrode (Example 1) are shown in FIG. 6. The FIG. 5 measurements were made at 600 mV with the 3-electrode system and FIG. 6 at 325 mV with the 2-electrode configuration.

Figure 7:
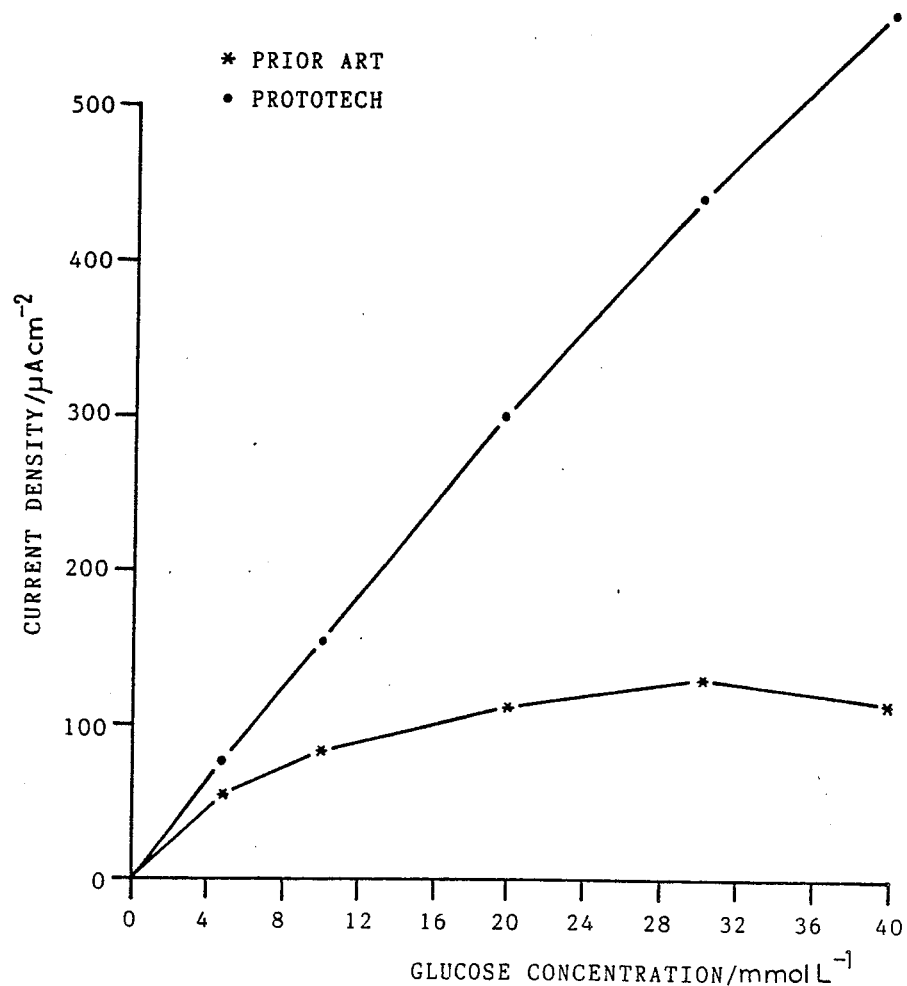
FIG. 7 shows the comparison between the response of a glutaraldehyde immobilised glucose oxidase electrode of this invention, and a glutaraldehyde immobilised glucose oxidase electrode according to the prior art.
Figure 8:
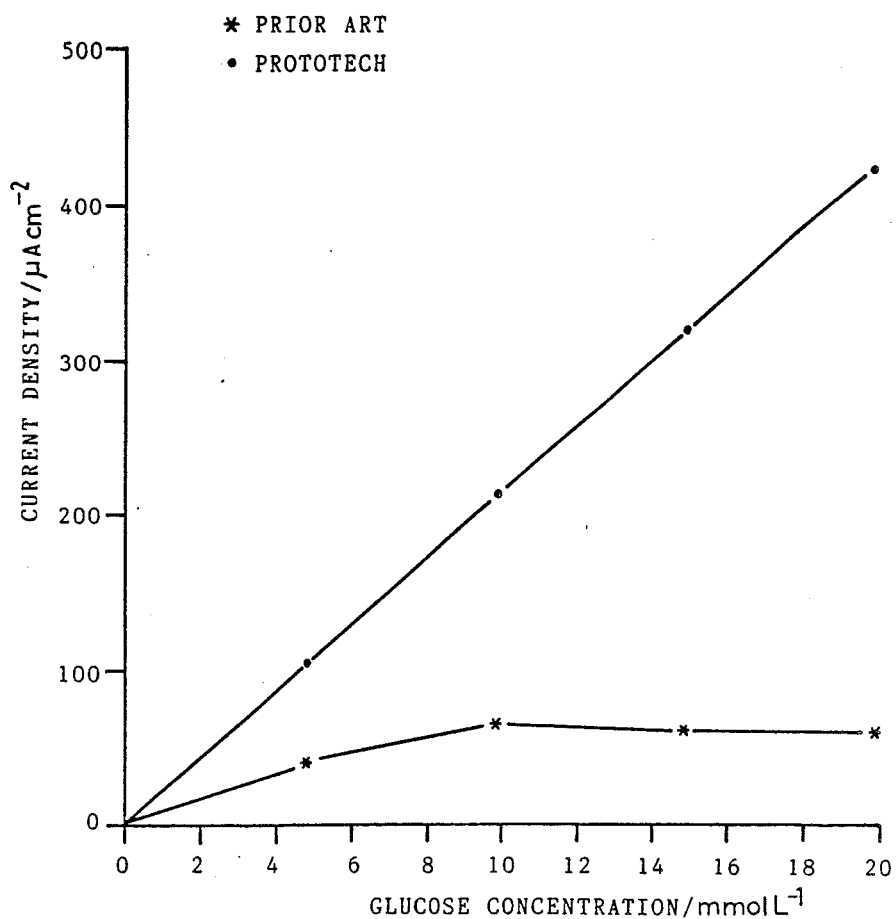
FIG. 8 corresponds to FIG. 7, but using carbodiimide immobilisation.
Figure 9:
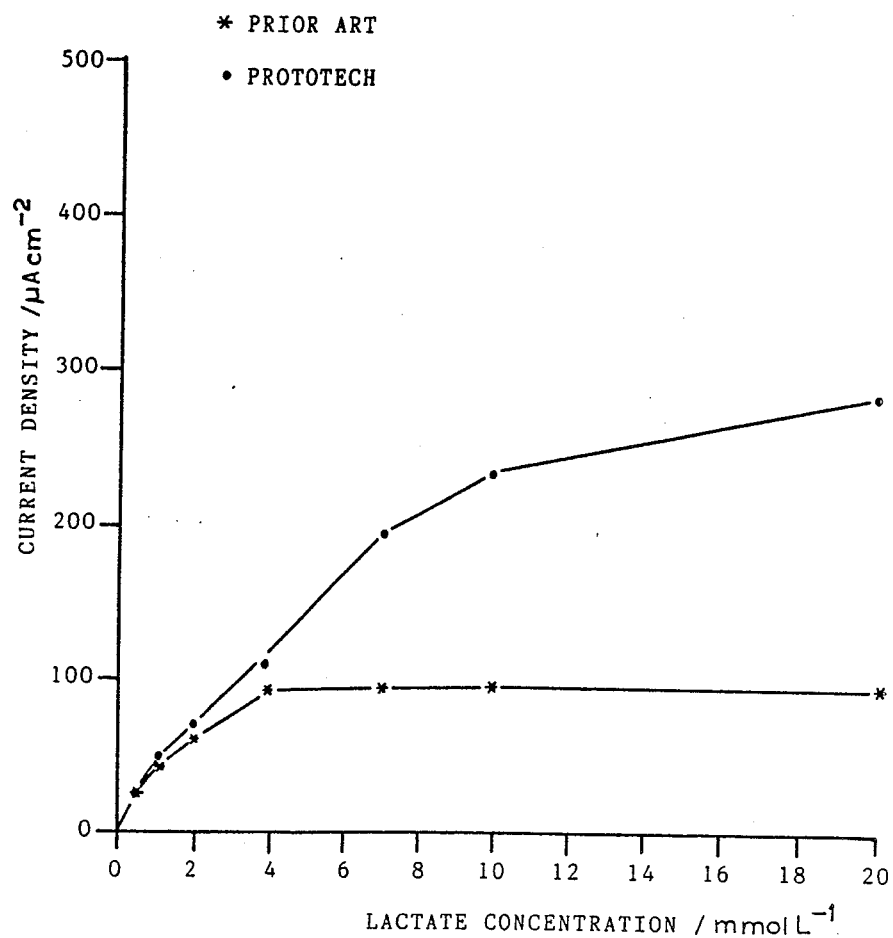
FIG. 9 shows the comparison between the response of a carbodiimide immobilised lactate oxidase electrode of this invention, and a carbodiimide immobilised lactate oxidase electrode according to the prior art.

Further comparisons between the response curves for the prior art (Example 1) electrodes and the present electrodes using different enzymes and different methods of immobilisation are shown in FIGS. 7 to 9, all measurements made at 325 mV.

Figure 10:
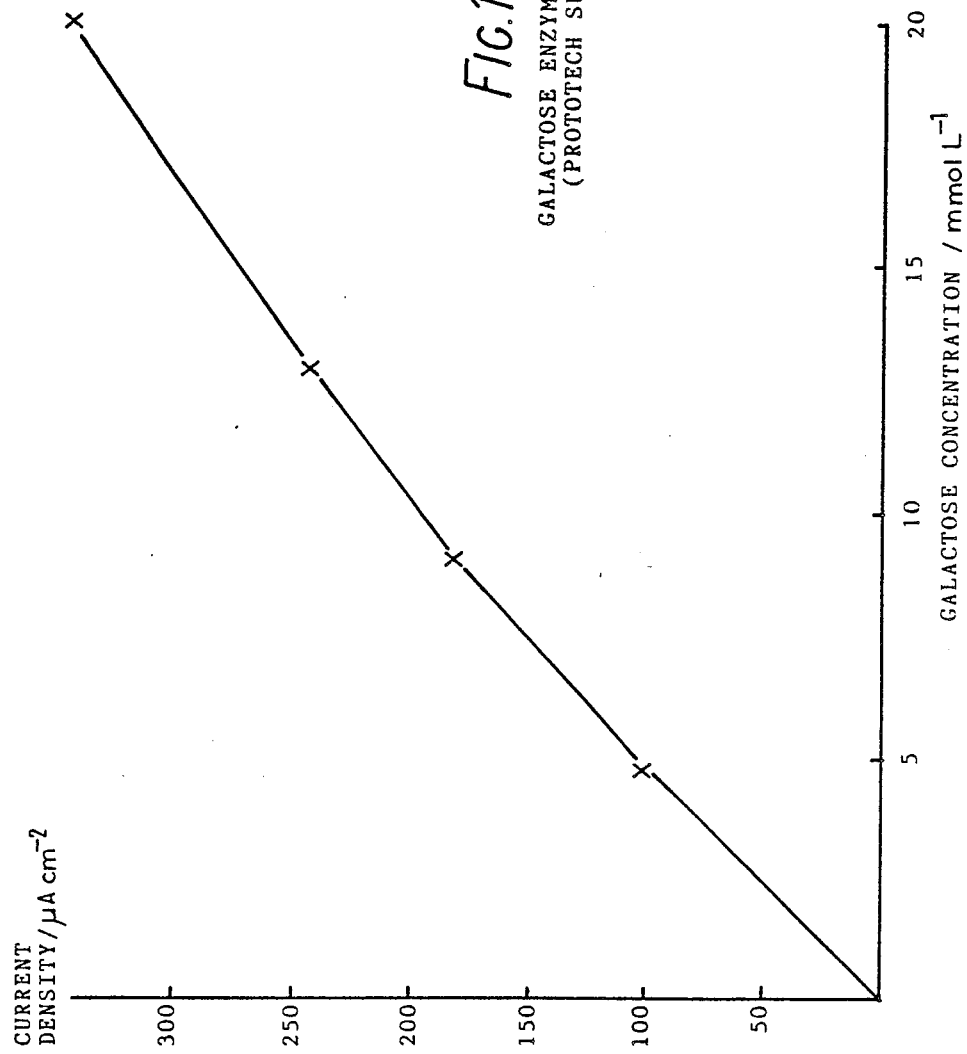
FIGS. 10 and 11 respectively show the response profile of the galactose oxidase and lactate oxidase electrodes according to this invention.
Figure 11:
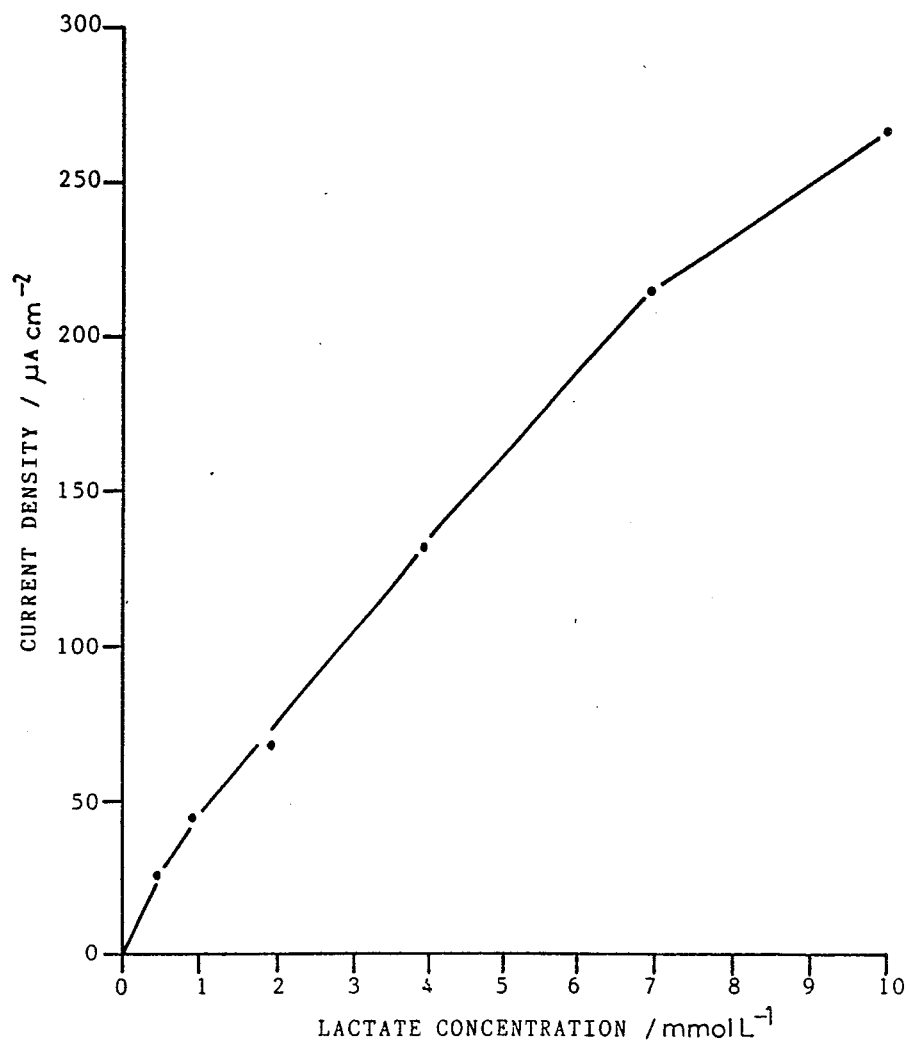
Figure 12:
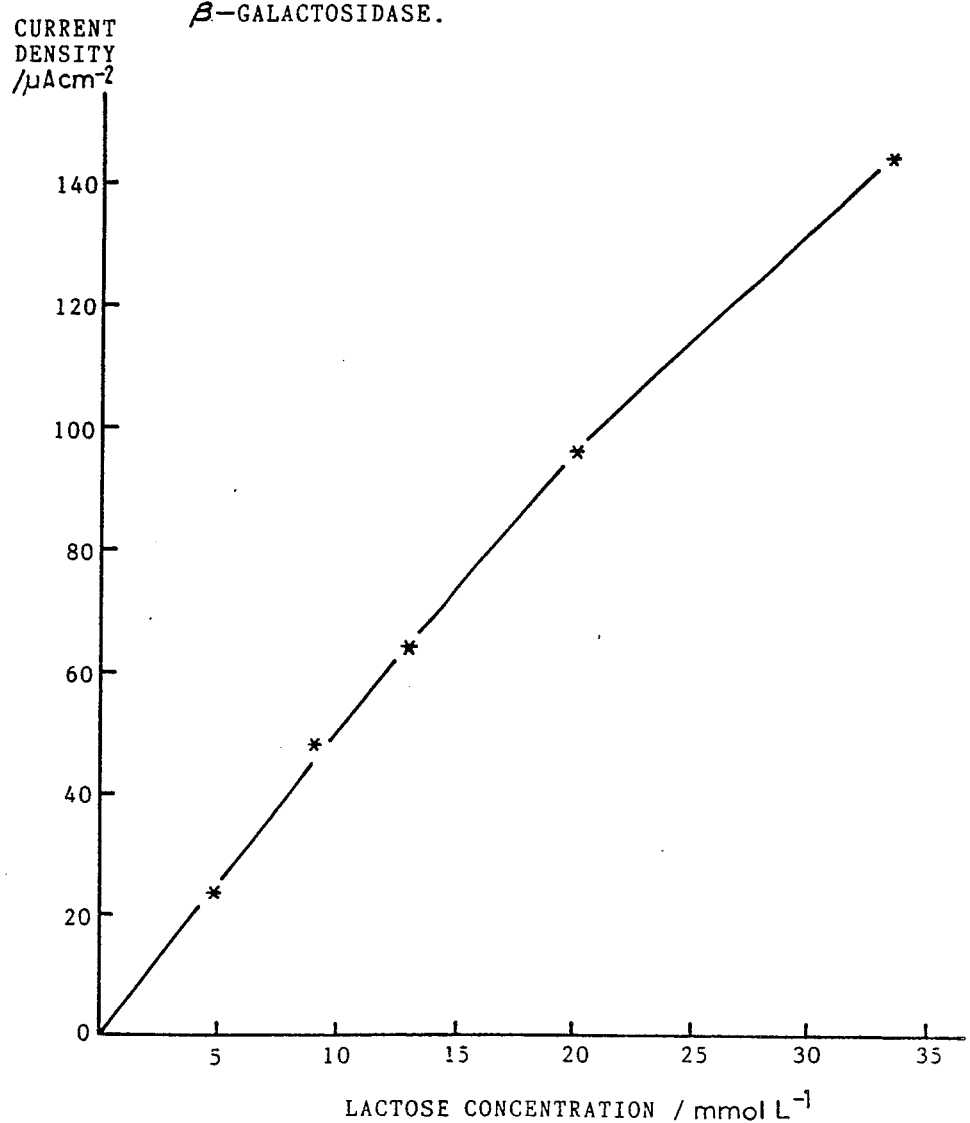
FIG. 12 shows the response profile of a combined glucose oxidase/beta-galactosidase electrode according to this invention.

The response curves for lactate, galatose and lactose (combined glucose oxidase and beta-galactosidase) are shown in FIGS. 10 to 12. These measurements were made at 600 mV.

Re-use of the Electrode: Suitability for Repeated Measurements

Under continuous load the electrodes of this invention showed exceptional longevity of a type which has not been recorded previously. This was illustrated by the following sequence of rigorous tests.

First a glucose oxidase electrode (Example 2) was set up in a closed cell and allowed to respond amperometrically to a stirred glucose solution (initial concentration 5 mM, initial current 100 $\mu$amp). It ran continuously for 18 hours, during which time the signal gradually fell to below 10 $\mu$amp. The total electricity produced corresponded to about 75% of that expected theoretically (on the basis of 2 electrons yielded per molecule of glucose). This experiment was immediately repeated with the same electrode by renewing the glucose solution, whereupon the initial current was re-established and the "run down" of substrate under continuous load gave identical results.

In a consecutive experiment, delivery of current using the same electrode was continued for a further 5.7 days, but with the supply of glucose solution provided by circulation from a large reservoir to maintain 5 mM concentration. The output fell slowly over a period of 100 hours, but then stabilised at 45 $\mu A$, which value was maintained for a further 40 hours. It is possible that some loosely bound enzyme became detached from the electrode base over this period (though there was no dependence of current output on stirring rate), or that some other conditioning effect operates.

After the long-term tests described above, the response of the electrode over a range of glucose concentration was tested as previously indicated. Although the signal amplitude was smaller than when freshly-prepared, the electrode gave a very satisfactory "step" function over the range 0 to 30 mM glucose, confirming that it had not suffered any deleterious effect as a result of the prolonged use under load. This conclusion was born out in three further tests after 1 week of storage (4° C.), after 8 weeks of storage, and after again running under load as before for an additional 4.7 days: the responses over a range of glucose concentration were unchanged.

These tests indicate that an electrode could be operated for a total time of at least 250 hours (over 15,000 minutes), thus giving the electrode material potentially an extremely long working life. The working lifetime of enzyme electrodes of the prior art is usually much shorter than those of the present invention, in many cases only a few hours: Turner, (1985) Proceedings Biotech 85 (Europe) Online Publications, Pinner, U.K., 181-192. For example, glucose electrodes based on ferrocene-coupled glucose oxidase generally have half lives of about 24 hours (Turner, loc. cit.), while Cass et al. (1984) Analyt. Chem. 56, 667-673 quote a total stable lifetime of 50 hours for the same electrodes. When an electrode was used for 50 consecutive measurements of 5 mM glucose solution the standard deviation was less than one percent.

Suitability for Continuous Monitoring

The level of final response recorded in the above-mentioned reusability rests (45 $\mu$amp in 5 mM glucose) remained unaffected by exposure to aerated solutions, and was the same after several weeks of further storage. The stability of current output from this electrode over 12 hours was checked in a controlled test using sterilised glucose solution under conditions designed to eliminate any loss of glucose from bacterial contamination. The signal was constant over the whole period, indicating that any effects of the initial "conditioning" of the electrode in a stirred and circulated solution over several days was complete. Such electrodes, suitably conditioned by this or some other appropriate conditioning/washing procedure, would find applications where continuous monitoring of glucose is required.

Batch Reproducibility

Provided that suitably "clean" preparative conditions are maintained, all electrodes made according to this invention work as described, giving good responses to glucose. Pairs of electrodes of identical size, prepared by the same procedure, gave closely concordant results (current responses within a few percent when tested under identical conditions). Furthermore, all electrodes so prepared had very long lifetimes and durability as indicated above, in contrast with glucose electrodes of the prior art. Thus the electrodes of this invention can be reliably stored and used for many weeks, whereas electrodes of the prior art often show much variability within a batch. For example, Turner, loc. cit., noted that although a few glucose oxidase electrodes within a batch were occasionally exceptionally long-lived (600 hours half-life), the majority had half-lives of about 24 hours. Therefore they could not be reliably used for periods very much longer than 24 hours.

Dependence of Response on Oxygen Concentration

To test the effect of dissolved oxygen a test cell was modified to include an oxygen electrode in addition to the glucose electrode. Experiments were carried out in which dissolved oxygen was swept out of the system by sparging with argon. Under these conditions the electrode of type A (above) gave a rapid response to additions of glucose, suggesting a mechanism largely independent of ambient oxygen concentration. Such a result, which is attributable to the particular characteristics of the electrode surface structure in combination with favourable enzyme immobilisation, has not been observed previously.

Figure 4:
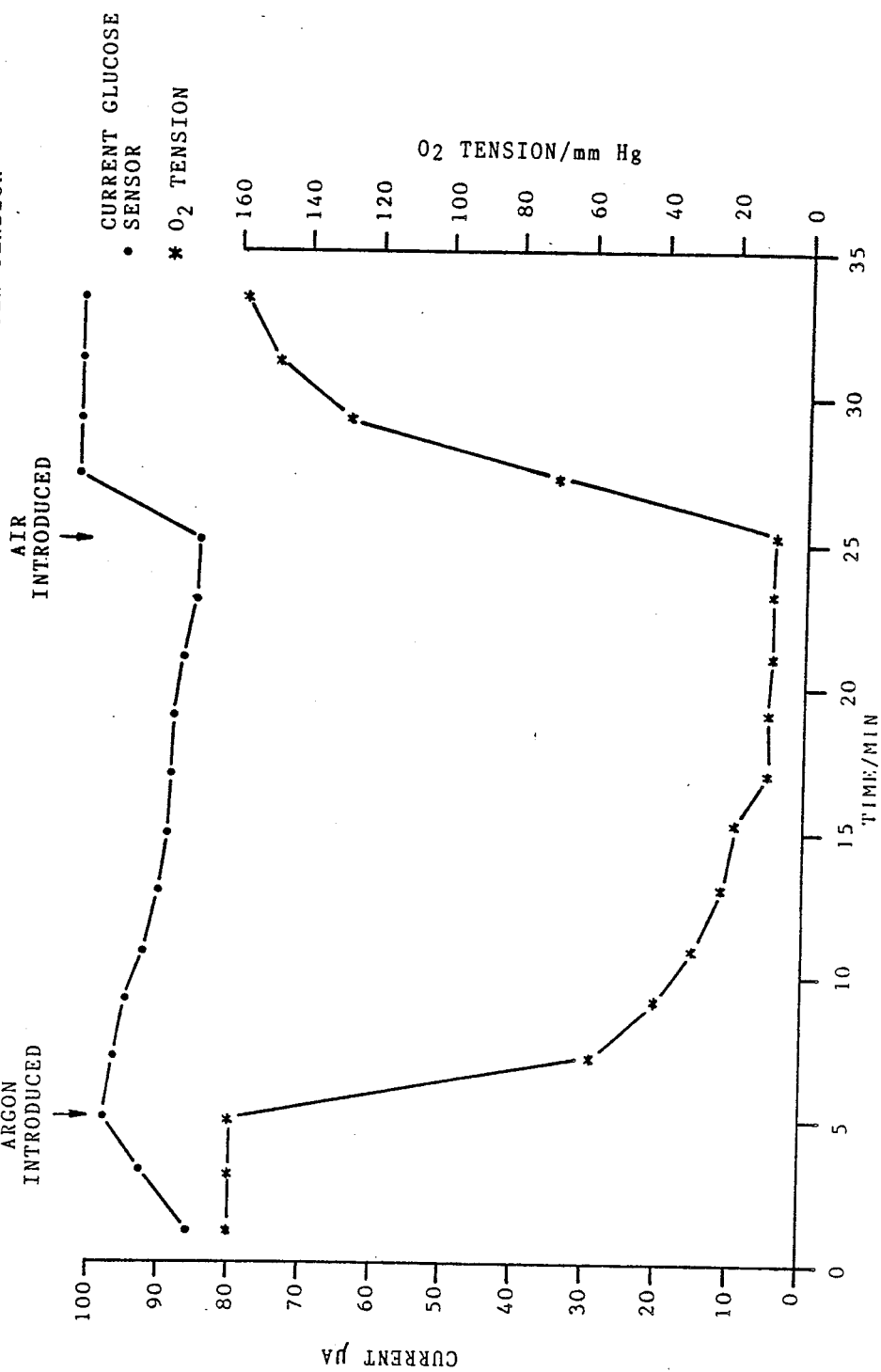
FIG. 4 is a graph illustrating the response of the glucose oxidase electrode under conditions of changing ambient oxygen tension.

In a further experiment (FIG. 4), the output signal of a type A electrode (prepared by Method A above) at 600 mV was monitored during continuous sparging with argon. Simultaneously measurements were made of oxygen tension in the sample. The results presented in FIG. 4 show a substantially constant current signal (the upper graph) substantially independent of the oxygen tension in the sample solution (the lower graph). In another test the signal was virtually unaffected over a 10 minute period, whereas the oxygen tension fell rapidly. Another electrode (prepared by Method B) showed a fall in current of under 5% over 3 minutes, during which time the oxygen had been depleted by 90%. An increase in current response is also observed when oxygen is re-introduced to the system, although this contribution is established relatively slowly. On prolonged purging with argon, the electrodes responded to only a limited range of glucose concentration, and it is possible that the presence of a trace of oxygen might be required for "triggering" that part of the enzyme function responsible for abstraction of hydrogen from the substrate. Also, it cannot be ruled out that oxygen adsorbed at the electrode (at a low concentration, and not detectable by the oxygen electrode) plays some role in this behaviour.

Enzyme Loading

Independent measurements of rate of glucose depletion and maximum current densities show that the amount of enzyme actively immobilised per electrode (type A) was equivalent to approximately 7 $\mu$g of active enzyme per square centimeter of electrode surface. (Little information is given in the literature on enzyme loadings of similar glucose oxidase based biosensors.) In the immobilisation procedures, it was found that even when the enzyme solution was diluted by as much as 10 times, very active electrodes could still be prepared.

Temperature Dependence of Response

Type A electrodes were tested over the concentration range 0 to 30 mM glucose at temperatures between 10° and 37° C. The temperature coefficient was 2 to 3% per degree (corresponding to an Arrhenius activation energy of ca. 24 kJ mol$^{-1}$). This compares with the value of 4% per °C. quoted for the ferrocene mediated biosensor (Cass et al, loc. cit.).

pH Dependence

A small dependence of response on pH was observed. But between pH 7.0 and 8.0 the response is virtually pH-independent, except at very high levels of glucose (>25 mM).

Response of Electrode Covered by Protective Membrane

A polycarbonate membrane was found to cause little change in the shape and magnitude of the electrode response in a stirred system. The response time in an unstirred system was about 20 seconds.

Use of Electrode for Analysis of Whole Blood Samples

The electrode with polycarbonate membrane was used satisfactorily for direct measurement of glucose in blood. Interference from ascorbate at 0.2 mmol/liter was about 2.5% of the total signal at a glucose level of 5 mmol/liter.

Use of Electrode in Different Configurations of Analytical Biosensor

The successful application of the enzyme electrode of this invention in a Rank-type cell using a modified Clark electrode as described above is demonstrated by the results discussed above. It has also been demonstrated that the electrode gives excellent results when used in other sensor modes, such as a probe.

For example, a 2 mm diameter probe of the type commonly used in many conventional electrodes was constructed in which the electrode was mounted on a wire and sealed into a glass tube. This could be inserted (with reference and counter electrodes attached) into stirred test solutions contained in a beaker or other container to make reliable measurements of glucose concentration without the need to eliminate atmospheric oxygen. From measurements with this and smaller probes of similar design, it was established that the current response of the electrodes in a solution of fixed glucose concentration is approximately proportional to the apparent area or weight of electrode.

Probes were also constructed in which the electrode was miniaturised (approx. 0.25 to 0.50 mm$^2$ area, 30 to 60 $\mu$g wt.). The wire mounting was covered in a plastic sleeve, and the sleeved probe was inserted in a catheter needle (1.5 mm diameter). The needle can be inserted through a rubber seal in a vessel (such as might be incorporated into a fermenter or similar apparatus, or a waste reservoir) and used as a probe-sensor for measuring the glucose concentration of a solution contained in the vessel. In this configuration the sensing electrode is protected by the surrounding needle at the time of insertion, but can also be pushed clear of the needle where necessary after the insertion stage.

Whereas miniature probes as described above gave signals typically in the range 1 to 10 $\mu$amp, accurate measurements in the range 1 to 100 namp are feasible with suitable instrumentation. Since signal currents in this range are supported by enzyme electrodes (of this invention) of very small size (approx. 0.005 mm$^2$ area, 1 $\mu$g wt.), such electrodes can be incorporated into fine needle microprobes such as would find application in catheter probes for in vivo measurements.

Whilst the mechanism underlying the operation of the electrodes of this invention is not fully understood, certain conclusions can be drawn based on the results obtained. Thus, it is known that the presence of active surface groups on carbon formed by surface oxidation at elevated temperatures lends itself to cross-linking reactions as required for immobilisation of enzymes, and the number and variety of such surface groups is probably increased when platinum (or other platinum group metal such as palladium) is present as a thin-layer surface catalyst (Kinoshita and Stonehart, (1977), Modern Aspects of Electrochemistry, No. 12, Ed. Bockris and Conway, Plenum Press, New York, 183-266). It is evident that differences in enzyme binding occur with different methods of immobilisation. (For example, many of the reported schemes utilise various amino acid residues for enzyme attachment, whereas enzymes bound with cyanuric chlorideactivated materials do so exclusively through their lysine residues; see Ianiello and Yacynych, (1981) Analyt. Chem. 53, 2090-2095.) Variations in the tertiary structures of enzymes produced upon immobilisation would not be expected to be identical for all immobilisation procedures, which may account for the large variations in enzyme activity and stability observed in this kind of work.

The extremely heterogeneous nature of the base electrode material used in this invention, in contrast to the layered, non-heterogeneous structure of the type of electrode described, for example, in Japanese Published Application No. 56-163447, maximises the probability of obtaining a multiplicity of cross-linkages of different types and orientations in an integrated three-dimensional structure. In the absence of cross-linking reagents, it also affords strong surface adsorption. The pores in the bound carbonaceous matrix allow the enzyme molecules to get "in and around" components of the matrix, which present a very large surface area to the enzyme, and allow conformations favourable for its stability and activity. (This is in contrast with the binding onto comparatively plane surfaces like platinum, "glassy" carbon or graphite, of much smaller surface area, which place constraints on the conformation, as indicated by previous work in the literature.) Moreover the extremely rapid response times of the electrodes of this invention (1 to 2 seconds) indicates an extremely rapid transfer of electrons to the electrode which requires not only high enzyme activity, but is assisted by a sufficiency of electron receptor sites on the electrode itself. These are provided by the high density of fine platinised carbon granules distributed over a very large area within the microstructure which maximise the probability of access of surface platinum growths to active sites on the enzyme.

To demonstrate the applicability of other resins as binders in enzyme electrodes according to the present invention, and other platinum group metals, glucose oxidase electrodes have been constructed using polyvinyl acetate as the binder, and palladium as the platinum group metal.

In the former case, a glucose oxidase electrode was constructed by immobilising glucose oxidase by Method A hereinbefore described onto the surface of a platinised carbon paper electrode constructed substantially as hereinbefore described (Example 2) but using 50% by weight of polyvinyl acetate as the binder in place of polytetrafluoroethylene.

Figure 13:
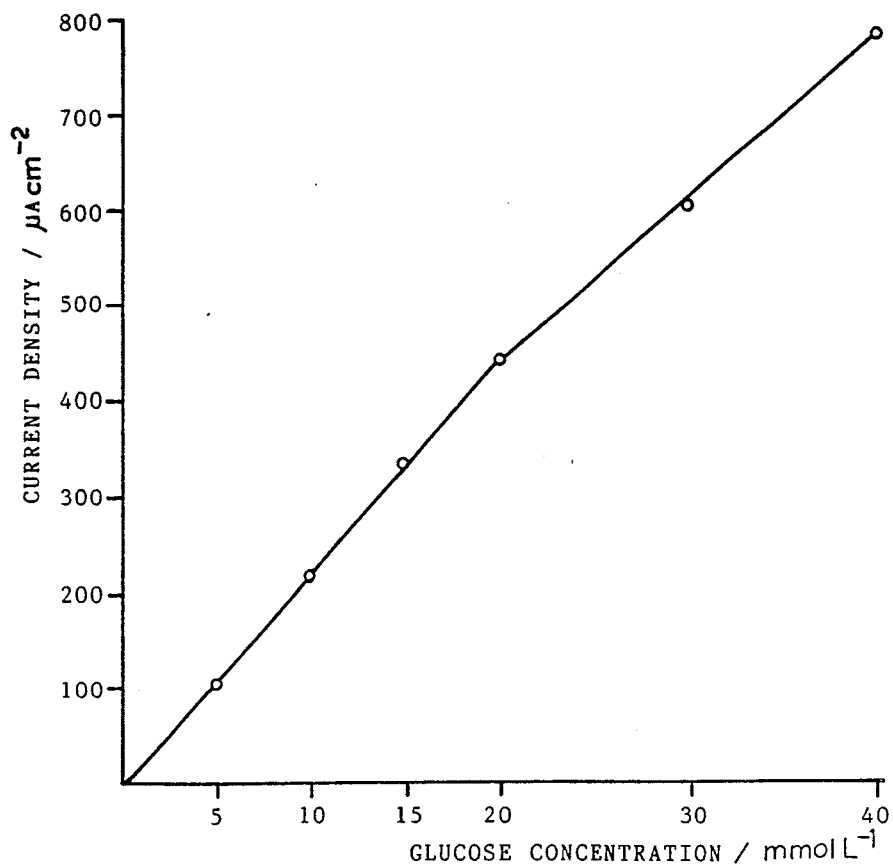
FIG. 13 shows the response profile of a glucose oxidase electrode according to the invention utilising polyvinyl acetate as the binder for the platinised carbon powder in place of polytetrafluoroethylene.

When tested using the same modified Rank electrode system at 325 mV, a substantially linear response was obtained as shown in FIG. 13.

In the latter case, a glucose oxidase electrode was constructed by immobilising glucose oxidase by Method A hereinbefore described onto the surface of a palladised carbon paper electrode prepared by depositing colloidal palladium onto the surface of a carbon powder (nominal particle size 30 nm: Vulcan XC-72) and subsequently bonding the palladised carbon powder as a thin layer (0.1 mm) onto the surface of an electrically conductive carbon paper using 50% by weight, based on the weight of the palladised carbon powder, of polytetrafluoroethylene as the binder.

Figure 14:
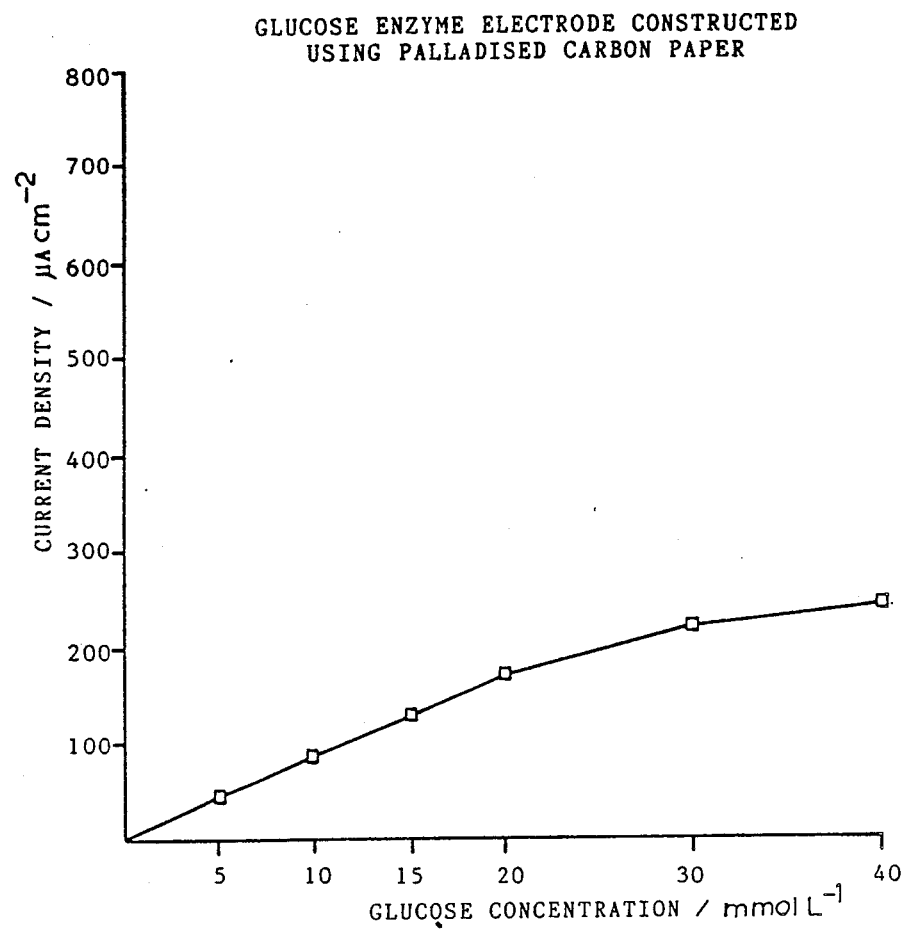
FIG. 14 shows the response profile of a glucose oxidase electrode according to the invention, in which the glucose oxidase is immobilised onto a carbon paper electrode comprising a surface layer of resin-bonded (polytetrafluoroethylene) palladised carbon powder.

A 2 mm diameter disc cut from the treated palladised carbon paper was mounted on the platinum contact of the 2-electrode cell described in FIG. 16, and tested for its response to glucose at 325 mV. The results are presented in FIG. 14 and again show a substantially linear response in terms of current density against glucose concentration.

In view of the express equivalence of Pt, Pd, Ru and Rh and other platinum group metals in gas diffusion electrodes taught in U.S. Pat. No. 4,293,396 and elsewhere it is to be expected that other platinum group metals, e.g. ruthenium and rhodium, will be effective as alternatives to platinum and palladium in the enzyme electrodes of this invention.

We claim:

1. An enzyme electrode for indicating amperometrically the catalytic activity of an enzyme in the presence of a liquid containing a substance acted upon by said enzyme and of an electric potential on the electrode, said electrode comprising
   (a) an electrically conductive support member comprising a porous electrically conductive layer formed of carbon particles in intimate surface contact with finely divided particles of a platinum group metal and bonded together by resin, said layer constituting a substantially heterogeneous porous substrate consisting essentially of resin-bonded metalized carbon particles with said metal particles distributed substantially uniformly therethroughout, and
   (b) a catalytically active quantity of said enzyme adsorbed or immobilized onto the surfaces of said porous substrate.

2. An enzyme electrode according to claim 1, said platinum group metal being present in the form of particles more finely divided than said carbon particles.

3. An enzyme electrode according to claim 1, said platinum group metal being present in the form of particles thereof adsorbed onto the surface of individual carbon particles, said metal particles having colloidal sizes in the range of about 15 to 25 Angstroms.

4. An enzyme electrode according to claim 1, the size of said carbon particles being in the range of about 50 to about 300 Angstroms.

5. An enzyme electrode according to claim 1, said platinum group metal being present in an amount of from 1 to about 20% of the weight of said carbon particles.

6. An enzyme electrode according to claim 1, said platinum group metal being platinum.

7. An enzyme electrode according to claim 1, said platinum group metal being palladium.

8. An enzyme electrode according to claim 1, said resin being a fluorocarbon resin or polyvinyl acetate.

9. An enzyme electrode according to claim 1, said resin being polytetrafluoroethylene.

10. An enzyme electrode according to claim 1, said enzyme being an oxidoreductase.

11. An enzyme electrode according to claim 1, said enzyme being glucose oxidase.

12. An enzyme electrode according to claim 1, said support member further comprising an electrically conductive base having said porous electrically conductive layer bonded thereto as a surface layer thereon.

13. An enzyme electrode according to claim 12, said base being an electrically conductive carbon paper.

14. An enzyme electrode according to claim 1, said enzyme being immobilized by covalent bonding or cross-linking of the enzyme on said surfaces.

15. An enzyme electrode according to claim 1, said enzyme having been immobilized onto said surfaces by treatment of said porous substrate with a solution of a carbodiimide reagent, a carbonyldiimidazole reagent or 1,6-dinitro-3,4-difluorobenzene and subsequent treatment of said substrate with a solution of said enzyme to effect covalent bonding of said enzyme on said surfaces.

16. An enzyme electrode according to claim 2, said enzyme having been immobilized onto said surfaces by treatment of said porous substrate with a solution of said enzyme and subsequent treatment of said substrate with glutaraldehyde to effect cross-linking of said enzyme on said surfaces.

17. An enzyme electrode according to claim 1, further comprising as a protective cover over said porous electrically conductive layer a microporous membrane permeable to said substance.

18. An enzyme electrode according to claim 17, said membrane being a polycarbonate membrane.

19. An enzyme electrode for indicating amperometrically the concentration in a liquid sample of a substance acted upon by an oxidoreductase, said electrode comprising
(a) an electrically conductive support member comprising a porous electrically conductive layer of carbon particles of about 30 to 500 Angstroms in size which have colloidal platinum particles of about 15 to 25 Angstroms in size deposited on their surfaces and as so platinized are bonded together by a fluorocarbon resin so that said layer constitutes a substantially heterogeneous porous substrate consisting essentially of resin-bonded platinized carbon particles with the particles of platinum distributed substantially uniformly therethroughout, the amount of said platinum particles being from 1 to about 20% of the weight of said carbon particles, and
(b) a catalytically active quantity of oxidoreductase adsorbed or immobilized onto the surfaces of said porous substrate.

20. An enzyme electrode according to claim 19, said substance being glucose and said oxidoreductase comprising glucose oxidase.

21. An enzyme electrode according to claim 19, said resin being polytetrafluoroethylene.

22. An enzyme electrode comprising an electrically conductive porous substantially heterogeneous layer consisting essentially of carbon particles metalized by particles of a platinum group metal adsorbed onto their surfaces, said metalized carbon particles being bonded together by resin so that said metal particles are distributed substantially uniformly throughout said layer, and a catalytically active quantity of oxidoreductase adsorbed or immobilized onto the surfaces of said porous layer.

23. An enzyme electrode according to claim 22, said oxidoreductase comprising glucose oxidase.

24. An enzyme electrode according to claim 23, said platinum group metal being platinum.

* * * * *